US011454623B2

(12) United States Patent
Weaver et al.

(10) Patent No.: US 11,454,623 B2
(45) Date of Patent: Sep. 27, 2022

(54) METHOD FOR QUANTITATIVELY ASSESSING STABILITY ADDITIVE PERFORMANCE AT FIELD DOSAGES

(71) Applicant: Baker Hughes, Houston, TX (US)

(72) Inventors: Carl E. Weaver, Conroe, TX (US); Roger D. Metzler, Sugar Land, TX (US); Koushik Gumaste, Houston, TX (US)

(73) Assignee: Baker Hughes Holdings LLC, Houston, TX (US)

( * ) Notice: Subject to any disclaimer, the term of this patent is extended or adjusted under 35 U.S.C. 154(b) by 533 days.

(21) Appl. No.: 16/594,833

(22) Filed: Oct. 7, 2019

(65) Prior Publication Data

US 2020/0116695 A1 Apr. 16, 2020

Related U.S. Application Data

(60) Provisional application No. 62/744,416, filed on Oct. 11, 2018.

(51) Int. Cl.

| | |
|---|---|
| ***G01N 33/28*** | (2006.01) |
| ***G01N 21/83*** | (2006.01) |
| ***E21B 49/02*** | (2006.01) |
| ***G01N 21/51*** | (2006.01) |

(52) U.S. Cl.

CPC ......... *G01N 33/2823* (2013.01); *E21B 49/02* (2013.01); *G01N 21/51* (2013.01); *G01N 21/83* (2013.01); *G01N 33/2835* (2013.01)

(58) Field of Classification Search

CPC .... G01N 21/83; G01N 21/51; G01N 33/2823; G01N 33/2835; E21B 49/02

See application file for complete search history.

(56) References Cited

U.S. PATENT DOCUMENTS

| | | | |
|---|---|---|---|
| 3,230,104 | A | 1/1966 | Falkenberg et al. |
| 3,249,451 | A | 5/1966 | Evans et al. |
| 3,662,953 | A | 5/1972 | Wiens |
| 5,443,632 | A | 8/1995 | Schilling |
| 5,667,578 | A | 9/1997 | Schilling |

(Continued)

FOREIGN PATENT DOCUMENTS

| | | | | |
|---|---|---|---|---|
| EP | 3147649 | A1 * | 3/2017 | ............ C10G 75/00 |
| WO | 9637545 | A1 | 11/1996 | |
| WO | 2011074003 | A2 | 6/2011 | |

OTHER PUBLICATIONS

Andersen, S., "Flocculation Onset Titration of Petroleum Asphaltenes," Energy and Fuels, 1999, vol. 13, pp. 315-322.

(Continued)

*Primary Examiner* — Rebecca C Bryant

(74) *Attorney, Agent, or Firm* — Crowe & Dunlevy, P.C.

(57) ABSTRACT

The impact of a stabilizing additive for treating oil-based fluids having destabilized solids, such as asphaltenes and polynuclear aromatics, may be quantitatively assessed, by determining the settling rate of flocculated destabilized solids in samples of untreated oil-based fluids and oil-based fluids treated with the stabilizing additive through the use of a turbidity meter or nephelometer while the field and quantifying the difference between the two settling rates to determine if a change in the amount of stabilizing additive applied to the oil-based fluid is necessary.

16 Claims, 3 Drawing Sheets

(56) References Cited

U.S. PATENT DOCUMENTS

| | | | | |
|---|---|---|---|---|
| 5,772,749 | A | 6/1998 | Schilling et al. | |
| 5,871,634 | A | 2/1999 | Wiehe et al. | |
| 5,997,723 | A | 12/1999 | Wiehe et al. | |
| 6,759,454 | B2 | 7/2004 | Stephens et al. | |
| 8,075,763 | B2 | 12/2011 | Sneddon et al. | |
| 8,236,564 | B2 | 8/2012 | Pauli et al. | |
| 8,646,964 | B1 | 2/2014 | Anderson et al. | |
| 8,876,921 | B2 | 11/2014 | Mcrobbie et al. | |
| 9,360,425 | B2 | 6/2016 | Jennings et al. | |
| 9,624,448 | B2 | 4/2017 | Joo et al. | |
| 10,125,306 | B2 | 11/2018 | Wang et al. | |
| 2002/0140925 | A1 | 10/2002 | Mougin | |
| 2003/0205507 | A1 | 11/2003 | Mikula et al. | |
| 2009/0051354 | A1 | 2/2009 | Kobayashi | |
| 2010/0022688 | A1 | 1/2010 | Stark et al. | |
| 2010/0163461 | A1 | 7/2010 | Wright et al. | |
| 2012/0125087 | A1 | 5/2012 | Sandu et al. | |
| 2015/0219614 | A1 * | 8/2015 | Respini | G01N 33/2823 208/178 |

OTHER PUBLICATIONS

Buckley, J.S et al., "Asphaltene Precipitation and Solvent Properties of Crude Oils," Petroleum Science and Technology, 1998, vol. 16 (384), pp. 251-285.

Stark, J. L., "Crude Oil Blending Effect on Asphaltene Stability in Refinery Fouling," Petroleum Science and Technology, 2003, 21, 569-579.

Garcia-Moralez, M. et al., "Effect of waste polymer addition on the rheology of modified bitumen," Fuel 2006 vol. 85, pp. 936-943.

PCT/US2012/064650; International Search Report dated Jan. 3, 2013.

Perez-Lepe, A. et al., "inftuence of the processing conditions on the rheological behavior of polymer-modified bitumen," Fuel 2003, vol. 82, pp. 1339-1348.

Turbiscan The Reference for Stability Analysis, Brochure, www.formulacation.com; date unknown, 4 pages.

ASTM Designation D7157-12: Standard Test Method for Determination of Intrinsic Stability of Asphaltene-Containing Residues, Heavy Fuel Oils and Crude Oils (n-Heptane Phase Separation; Optical Detection, Apr. 2017, 1-9.

* cited by examiner

METHOD FOR QUANTITATIVELY ASSESSING STABILITY ADDITIVE PERFORMANCE AT FIELD DOSAGES

CROSS-REFERENCE TO RELATED APPLICATION

This application claims the benefit of Provisional Patent Application No. 62/744,416 filed Oct. 11, 2018, which is incorporated by reference herein in its entirety.

TECHNICAL FIELD

The present disclosure relates to quantitatively assessing the impact of a stabilizing additive for treating oil-based fluids having destabilized solids, such as asphaltenes and polynuclear aromatics, by determining the settling rate of the destabilized solids in samples of untreated oil-based fluids and oil-based fluids treated with the stabilizing additive while in the field.

BACKGROUND

As world reserves of light, sweet crudes diminish and worldwide consumption of oil increases, refiners seek methods for extracting useful products such as gasoline and fuel oils from heavier crude resources. While not as desirable and easy to process, extensive reserves in the form of "heavy crudes" exist in a number of countries, including Western Canada, Venezuela, Russia, the United States, and elsewhere.

Crude oils and their distillates are often difficult to store and process because of their viscosity and the presence of destabilized solids, such as asphaltenes, polynuclear aromatics, coke, coke precursors, which can become destabilized in the oil-based fluid and these destabilized solids agglomerate and then precipitate or settle.

Asphaltene precipitation and deposition, for example, can cause problems in subterranean reservoirs, upstream production facilities, mid-stream transportation facilities, refineries, and fuel blending operations. When asphaltenes precipitate from crude oil, they can foul equipment and reduce the quality of the products being refined. Asphaltene deposition is a well-known problem affecting all aspects of petroleum production and processing. In addition, crude oils containing high or low levels of asphaltenes can be destabilized while blending and processing, causing fouling, formation of sludge and corrosion creating operational impacts that reduce production rates and increase energy consumption, repairs, cleaning, and cost aggravations associated with all these effects.

Remedial efforts may be employed to mitigate the instability of the oil-based fluid caused by precipitating agglomerated solids. At least one such remedial effort includes adding a stabilizing additive to the oil-based fluid. However, current methods employed do not provide the ability to quantitatively assess the impact of such additives on the settling rate of any destabilized solids while in the field, making it difficult to quickly and easily ascertain if more or less stabilizing additive needs to be applied to the oil-based fluid.

Thus, it would be desirable to develop better methods of determining the treatment performance of a stabilizing additive for treating oil-based fluids having destabilized solids at field dosages.

SUMMARY

There is provided, in one form, a method for evaluating the impact of a stabilizing additive on the settling rate of destabilized solids, like asphaltenes and polynuclear aromatics, in an oil-based fluid. The method involves preparing samples of an oil-based fluid containing flocculated destabilized solids and a field dosage amount of a stabilizing additive and an oil-based fluid containing flocculated destabilized solids with no stabilizing additive via solvent dosing titration and then measuring the difference in the settling rate of the flocculated destabilized solids in each sample to evaluate the performance of the stabilizing additive.

The method may further include implementing a change to the amount of stabilizing additive applied to the oil-based fluid based upon quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive.

In another form, the settling rate is measured using a turbidity meter or nephelometer located in the field.

DETAILED DESCRIPTION

Figure 1:
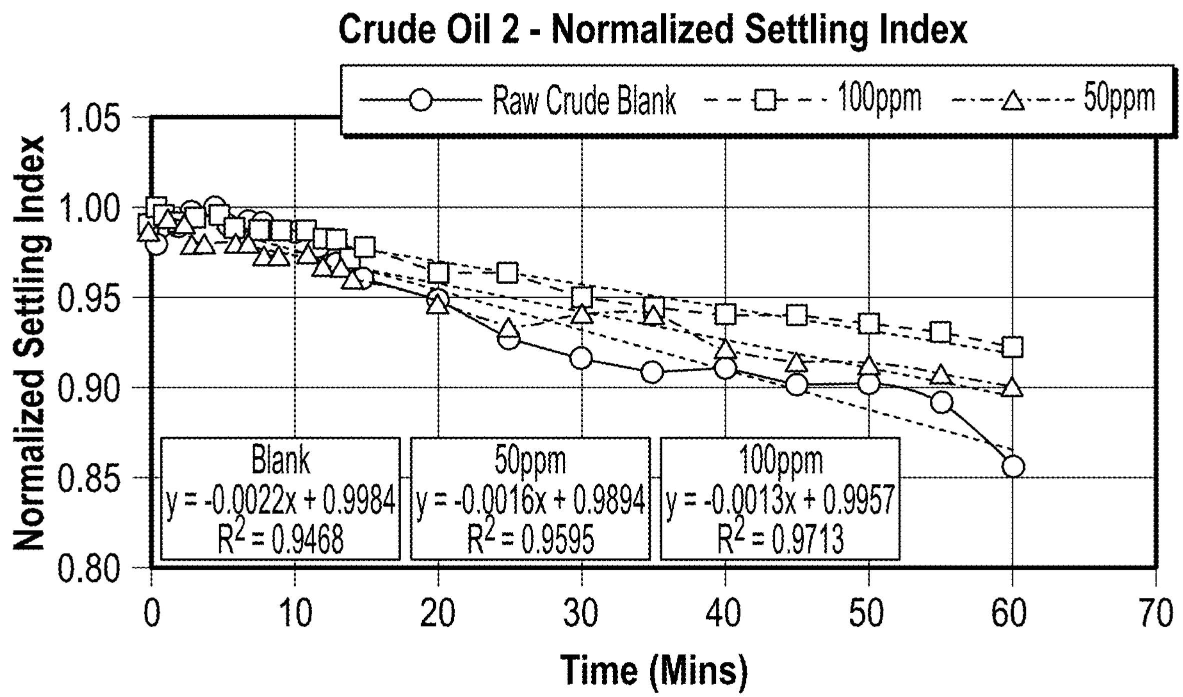
FIG. 1 is a graph comparing the normalized settling index for asphaltene flocs in a sample of crude oil containing no stabilizing additive, the normalized settling index for asphaltene flocs in a sample of crude oil containing 50 ppm of a stabilizing additive, and the normalized settling index for asphaltene flocs in a sample of crude oil containing 100 ppm of a stabilizing additive.

It has been discovered that the performance of an additive applied to an oil-based fluid to curb or prevent the destabilization of the fluid and other problems caused by the flocculation and precipitation of solids and particulates in the oil-based fluid may be quantitatively assessed in the field.

This quantitative assessment may be accomplished, in one embodiment, by a method having the following steps: (1) preparing a sample of an oil-based fluid containing flocculated destabilized solids and a field dosage amount of a stabilizing additive and preparing a sample of an oil-based fluid containing flocculated destabilized solids with no stabilizing additive; (2) measuring the change in turbidity over time of each sample to determine a settling rate of the flocculated destabilized solids in each sample; and (3) quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive.

In a non-limiting embodiment, the oil-based fluid may be or include, but is not limited to, crude oil, fuel oil, atmospheric residua, vacuum, residua, distillation residua, quench oil, visbreaker tar, H-Oil process stream, LC Fining process stream, and fluidized catalytic cracker slurry. In another non-limiting embodiment, the oil-based fluid may be or include a blend of at least two oil-based fluids, which may be the same oil-based fluids or different oil-based fluids. For example, the blend may be, but is not limited to, two or more crude oils blended together, or the blend may be two or more distillation residua fluids, etc.

The types of destabilized solids that are present in oil-based fluids that often prompt treatment to prevent the destabilization of the fluids and other problems that may occur in the production, transportation, storage, and process of the oil-based fluids are numerous. Examples of such destabilized solids include, without limitation, asphaltenes, polynuclear aromatics, coke, coke precursors, and combinations thereof.

With regard to the stabilizing additive, any stabilizing additive known to be useful to those of ordinary skill in the art may be employed with the method. For example, in one non-limiting embodiment, the additive may be prepared from a formulation including: a first component selected from the group consisting of (alkoxylated)-(di or tri)-alkyl phenol—aldehyde (amine) resins; α-Olefin—maleic anhydride co-polymers and grafted polymers including half ester/amide and full ester/amide derivatives; and combinations thereof. Such a formulation may also include a second component that may be or include, but is not limited to, polyamines, amidoamines, imidazolines, and combinations thereof. Other suitable stabilizing additives useful for treating oil-based fluids include but are not limited to, alkyl phenolic resins, alpha-olefin maleic copolymers, 4-nonylphenol formaldehyde resin, and combination thereof.

For purposes of this disclosure, "field dosage amount" is defined to mean the range of concentration or range of amounts of stabilizing additive that are normally applied to oil-based fluids that contain destabilized solids of the kinds described herein to prevent the destabilization of the fluids and other problems that may occur in the production, transportation, storage, and process of the oil-based fluids when the solids begin to flocculate (i.e. agglomerate). In one form of this method, the field dosage amounts may range from about 1 ppm independently to about 500 ppm independently, and alternatively, from about 10 ppm independently to about 50 ppm independently. As used herein with respect to a range, "independently" means that any threshold may be used together with another threshold to give a suitable alternative range, e.g. about 10 ppm to about 500 ppm is also considered a suitable alternative range.

The samples referred to in step (1) of the method set forth above may be prepared by, as non-limiting example: titrating a reference sample of an oil-based fluid containing destabilized solids and a field dosage amount of a stabilizing additive and separately titrating a reference sample of an oil-based fluid containing destabilized solids with no stabilizing additive with doses of a paraffinic solvent until there is flocculation of the destabilized solids; after flocculation of the destabilized solids, extracting a portion from each titrated oil-based fluid sample; and mixing each extracted portion with a cycloparaffin for purposes of, in some instances, dispersing the destabilized solid flocs or agglomerates present in each extracted sample.

In another form, step (1) of the method set forth above may also be carried out by Baker Hughes Field Asphaltene Stability Index Test (ASIT) service technology. This process involves destabilized a crude oil sample by titration with a "non-solvent" (a straight chain-alkane solvent) at a constant rate. The transmittance of the laser is monitored throughout the procedure. Initially, the transmittance increases due to the titrant addition to the sample, which causes the density of the sample to decrease. Once asphaltene flocculation begins, transmittance through the sample decreases as the flocculated asphaltenes block and defract the laser. On a plot of transmittance verses volume of titrant added, expressed as Asphaltene Stability Index (ASI), which includes a mass/volume balance calculation, the inflection point corresponds to the initial onset of asphaltene precipitation. The amount of titrant required to cause this precipitation indicates the stability of the sample. The decline in transmittance can either be sharp or gradual. A sharp decline denotes a significant amount of asphaltene precipitation, which correlates to a higher level of sludge formation once a flocculation point had been reached. A more gradual decline means only a small amount of the asphaltenes were beginning to fall out of solution and that a constant destabilized force was required to complete the precipitation of asphaltenes.

In a non-limiting embodiment, the flocculation titration method may be an optical method using a coherent light source that allows measuring the transmittance through the sample and relates especially to measuring the onset flocculation of the destabilized solids (e.g. asphaltenes) within an oil-based fluid sample. Changes in the sample transmittance (such as foulant aggregation and precipitation) may be induced via temperature and/or via adding a solvent. The transmittance changes versus temperature and/or solvent addition may be measured with high degree of sensitivity and repeatability.

The solvent for the solvent dosing during the flocculation titration may be or include, but is not limited to, cetane, heptane, xylene, toluene, hexane, pentane, dodecane, a paraffinic solvent having a solubility range of about 6.8 to 7.2 $(cal/cm^3)^{1/2}$, and combinations thereof. The three dilution approach may be used where oil-based fluid samples of known amounts may be diluted at three different ratios: 1:1, 1:1.5, 1:2, and so on until destabilized solids (e.g. asphaltenes or polynuclear aromatics) agglomerate (i.e. flocculate) and begin precipitating from the oil-based fluid sample in a non-limiting embodiment.

Cycloparaffins are utilized in preparing the samples because it has been shown that they have a more neutral effect in disrupting solids solubility. A non-limiting example of a suitable cycloparaffin for use in the sample preparation is cyclohexane.

Regarding step (2) above, measuring the change in turbidity over time of each sample to determine a settling rate of the flocculated destabilized solids in each sample may be conducted using turbidimetry and nephelometry.

Turbidimetry is a process of measuring the loss of intensity of transmitted light due to the scattering effect of particles suspended therein. As agglomerates (i.e. flocs) in an oil-based fluid being to settle or precipitate, the turbidity measurements decrease over time because more light is allowed to pass through the non-aqueous phase. Light may be passed through a filter creating a light of known wavelength that is then passed through a cuvette containing a solution. The turbidity measurements may be accomplished, without limitation, with the following turbidimetric methods: turbidimetry, nephelometry, infrared spectroscopy by attenuated total reflectance (ATR), and combinations thereof. In one embodiment, the turbidity measurements are made using a portable or hand-held turbidity meter may be one that can be used in the field. For purposes of this disclosure, "in the field" is defined to mean any place the oil-based fluid is produced or processed.

Nephelometry uses a nephelometer to measure the concentration of suspended particulates in a liquid or gas colloid by employing a light source and a light detector set to one side (e.g. 90 degrees) of the light source beam. Particle density may be a function of light reflected into the detector from the particles. The reflected light may be dependent upon properties of the particles, such as shape, color, and reflectivity.

In a non-restrictive embodiment, the method may further include implementing a change to the amount of stabilizing additive applied to the oil-based fluid based upon the quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive. The ability to measure and quantify the change or difference in the settling rate of the flocculated destabilized solids in the sample of the oil-based fluid having a field dosage amount of stabilizing additive and the settling rate of the flocculated destabilized solids in the sample of the oil-based fluid having no stabilizing additive can allow the evaluation or assessment of the performance or impact of the stabilizing additive.

In another non-limiting embodiment, a change to at least one production, storage, transportation or refinery process may be necessitated pending the results of the determination of the settling rate of the flocculated destabilized solids in the sample of the oil-based fluid having a field dosage amount of stabilizing additive and the settling rate of the flocculated destabilized solids in the sample of the oil-based fluid having no stabilizing additive. Such change(s) may be or include, but is not limited to, adding an additional feed stream to the oil-based fluid to stabilize the oil-based fluid, adding an additive to the oil-based fluid, adding a different demulsifier to the oil-based fluid than any demulsifier already present in the oil-based fluid, changing a temperature of the oil-based fluid, changing a water feed rate of a unit within the refinery process, and combinations thereof. Other non-limiting examples of changes that may occur include changing the oil-based fluids to be blended, changing the oil-based fluid mixing order, etc. In one non-limiting embodiment of the method of the application, the operator may elect to change operating parameters including, but not limited to changing fluid flow velocities, changing unit operating temperatures, changing unit residence times, and the like.

In yet a further non-limiting embodiment, the operator may elect to make changes by mixing at least two feed streams to bring the ratio of the settling rates of the combined stream into the pre-determined range.

The invention will be further described with respect to the following Examples, which are not meant to limit the invention, but rather to further illustrate the various embodiments.

EXAMPLES

Figure 3:
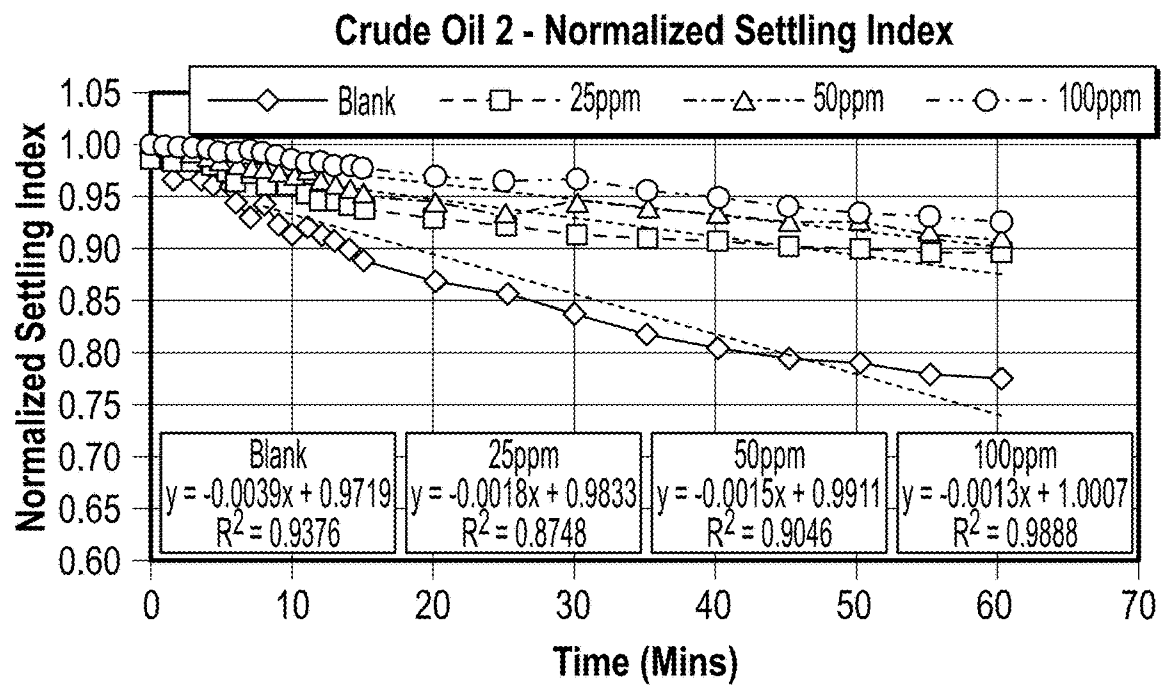
FIG. 3 is a graph comparing the normalized settling index for asphaltene flocs in a sample of crude oil containing no stabilizing additive, the normalized settling index for asphaltene flocs in a sample of crude oil containing 25 ppm of a stabilizing additive, the normalized settling index for asphaltene flocs in a sample of crude oil containing 50 ppm of a stabilizing additive, and the normalized settling index for asphaltene flocs in a sample of crude oil containing 100 ppm of a stabilizing additive.

Now turning to the Figures, FIGS. 1 and 3 are graphs comparing the normalized settling index ("NSI") values for asphaltene flocs in samples of crude oil containing no stabilizing additive and the NSI values for asphaltene flocs in samples of crude oil containing various amounts of an alkyl phenol resin stabilizing additive. The NSI value is based on the turbidity measure that is normalized to the highest possible turbidity measurement. The unit of measurement of turbidity is an NPU (nephelometric turbidity unit).

As FIGS. 1 and 3 show, the NSI values of asphaltene flocs in the samples of crude oil treated with highest amounts of the additive remain consistently higher than the NSI values for the samples of crude oil containing no or lower amounts of stabilizing additive. These results would be compatible with the principles of Stoke's law, under which it would be expected that smaller particles or agglomerates/flocs would settle more slowly than larger ones.

Figure 2:
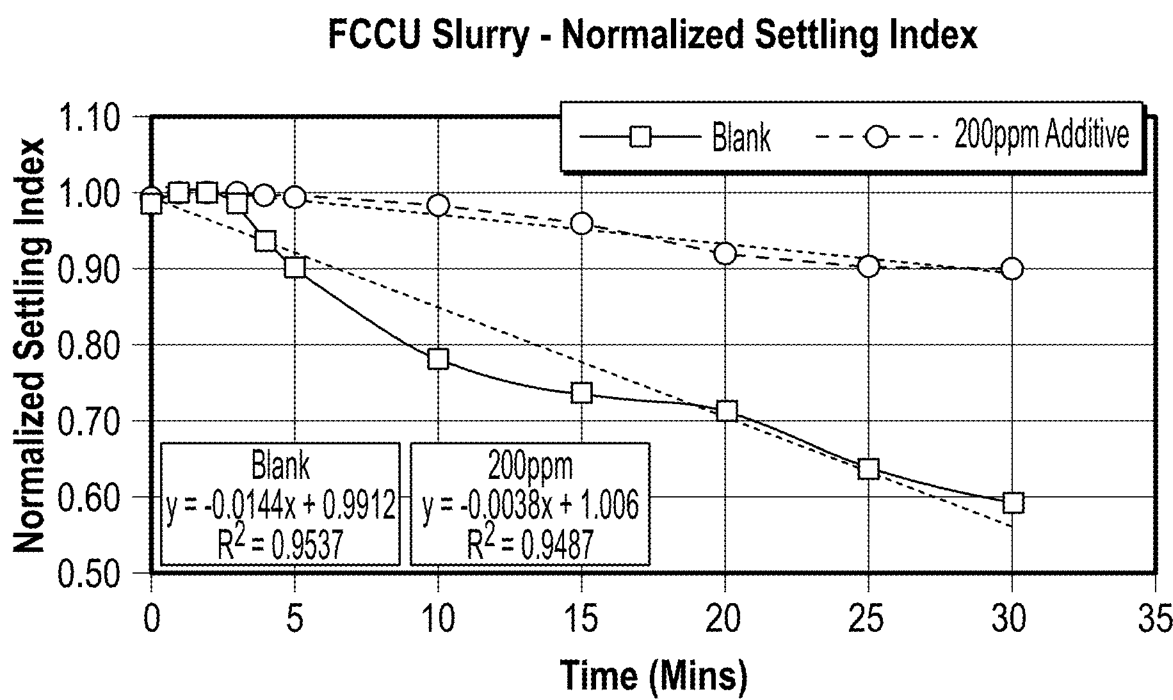
FIG. 2 is a graph comparing the normalized settling index for polynuclear aromatic flocs in a sample of FCC slurry containing no stabilizing additive and the normalized settling index for polynuclear aromatic flocs in a sample of FCC slurry 200 ppm of a stabilizing additive.

The same effect was shown when a sample of FCC slurry was tested. FIG. 2 is a graph comparing the NSI values for polynuclear aromatic flocs in a sample of FCC slurry containing no stabilizing additive and the NSI values for polynuclear aromatic flocs in a sample of FCC slurry 200 ppm of an alkyl phenol resin stabilizing additive. Again, it is shown that the flocs in the treated sample don't settle as quickly as the flocs in the untreated sample.

Figure 4A:
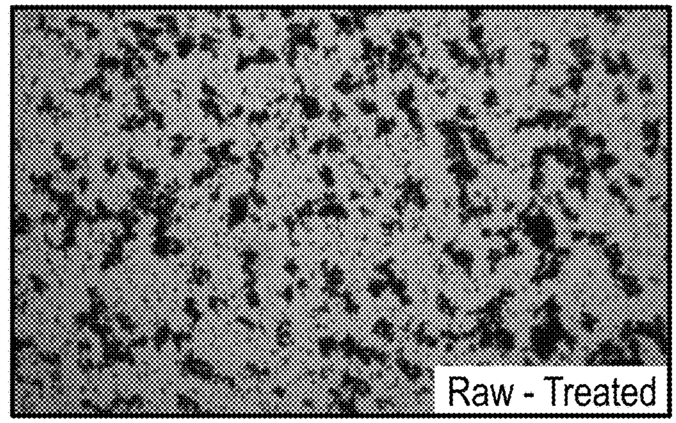
FIGS. 4A and 4B are microscope photographs showing the asphaltene flocs in sample of raw crude oil containing no stabilizing additive and the asphaltene flocs in a sample of raw crude oil containing 15 ppm of an alkyl phenol resin.
Figure 4B:
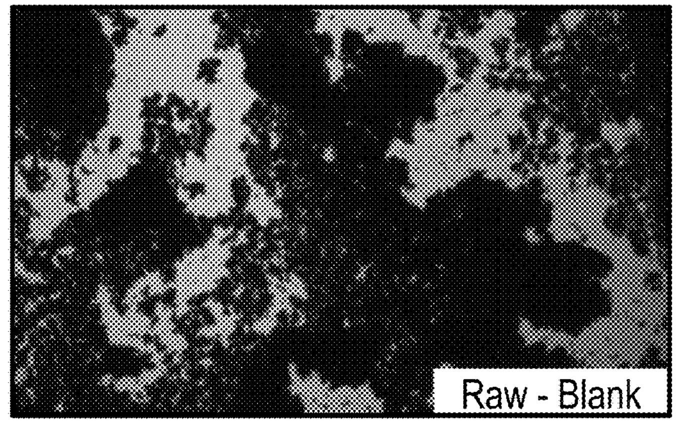

FIG. 4 shows a set of microscope photographs depicting the asphaltene flocs in sample of raw crude oil containing no stabilizing additive, on the right, and the asphaltene flocs in a sample of raw crude oil containing 15 ppm of an alkyl phenol resin stabilizing additive, on the left. These photographs illustrate that the asphaltene flocs in the treated sample are much smaller and thus would be associated with higher turbidity measurements than the asphaltene flocs in the untreated sample.

Figure 5:
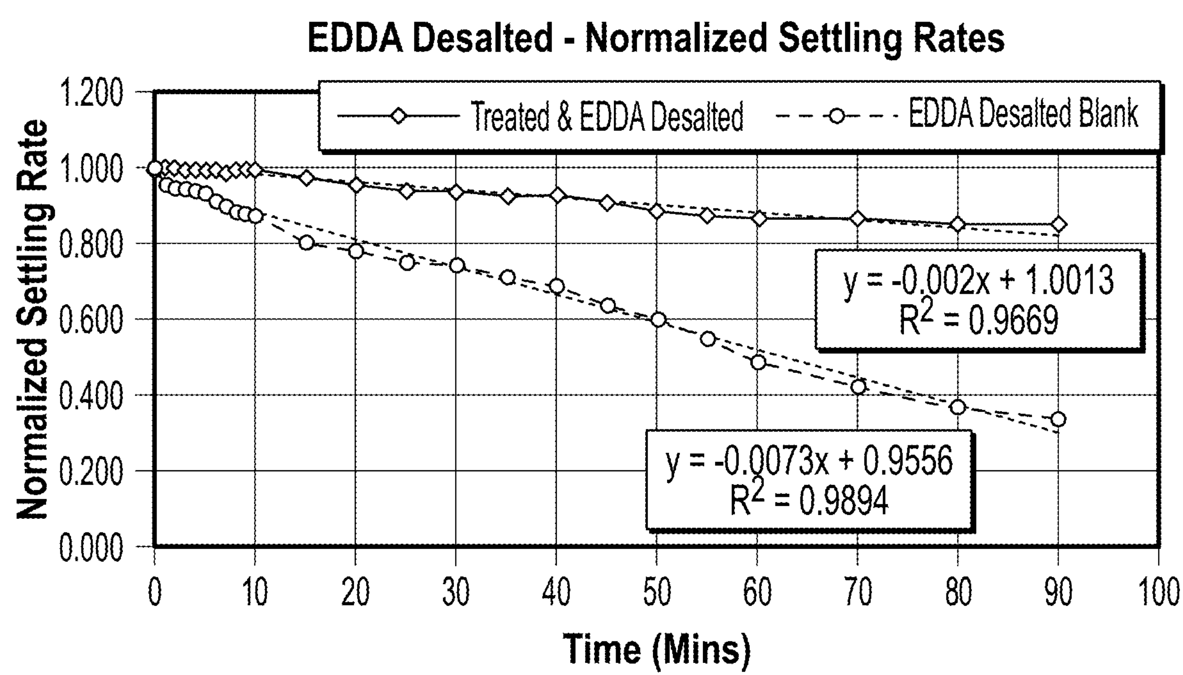
FIG. 5 is a graph comparing the normalized settling rates for asphaltene flocs in a sample of EDDA desalted crude oil with a primary demulsifier containing no stabilizing additive and a sample of sample of EDDA desalted crude oil with a primary demulsifier containing 15 ppm of a stabilizing additive.

Finally, FIG. 5 reflects the data obtained when samples of desalted crudes prepared by an Electrostatic Dehydration Demulsification Apparatus ("EDDA") containing asphaltene flocs were evaluated. The graph in FIG. 5 compares the normalized settling rates for asphaltene flocs in a sample of EDDA desalted crude oil with an oxyalkylated alkylphenolic resin primary demulsifier and no stabilizing additive and a sample of sample of EDDA desalted crude oil with the same primary demulsifier containing 15 ppm of an alkyl phenol resin stabilizing additive.

Here too, it is indicated that the flocs in the treated sample don't settle as quickly as the flocs in the untreated sample In the foregoing specification, the invention has been described with reference to specific embodiments thereof, and has been described as effective in providing methods for determining a settling rate of at least one foulant in oil-based fluids. However, it will be evident that various modifications and changes can be made thereto without departing from the broader spirit or scope of the invention as set forth in the appended claims. Accordingly, the specification is to be regarded in an illustrative rather than a restrictive sense. For example, specific oil-based fluids, solvents, stabilizing additives, destabilized solids, turbidimetry or nephelometry methods, and the like falling within the claimed parameters, but not specifically identified or tried in a particular method, are expected to be within the scope of this invention.

The present invention may suitably comprise, consist or consist essentially of the elements disclosed and may be practiced in the absence of an element not disclosed. For instance, the method for determining the impact of a stabilizing additive on the settling rate of destabilized solids in an oil-based fluid may consist of or consist essentially of: preparing a sample of an oil-based fluid containing flocculated destabilized solids and a field dosage amount of a stabilizing additive and preparing a sample of an oil-based fluid containing flocculated destabilized solids with no stabilizing additive; measuring the change in turbidity over time of each sample to determine a settling rate of the flocculated destabilized solids in each sample; and quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive.

The words "comprising" and "comprises" as used throughout the claims, are to be interpreted to mean "including but not limited to" and "includes but not limited to", respectively.

as used herein, the singular forms "a," "an," and "the" are intended to include the plural forms as well, unless the context clearly indicates otherwise.

To the extent used herein, the term "and/or" includes any and all combinations of one or more of the associated listed items.

As used herein, the term "about" in reference to a given parameter is inclusive of the stated value and has the meaning dictated by the context (e.g., it includes the degree of error associated with measurement of the given parameter).

What is claimed is:

1. A method for determining the impact of a stabilizing additive on the settling rate of destabilized solids in an oil-based fluid comprising:

preparing a sample of an oil-based fluid containing flocculated destabilized solids and a field dosage amount of a stabilizing additive and preparing a sample of an oil-based fluid containing flocculated destabilized solids with no stabilizing additive; and measuring the change in turbidity over time of each sample to determine a settling rate of the flocculated destabilized solids in each sample; and quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive to assess performance of the stabilizing additive.

2. The method of claim 1, wherein the step of preparing samples of an oil-based fluid containing flocculated destabilized solids and a field dosage amount of a stabilizing additive and an oil-based fluid containing flocculated destabilized solids with no stabilizing additive comprises:

titrating an oil-based fluid containing destabilized solids and a field dosage amount of a stabilizing additive and an oil-based fluid containing destabilized solids with no stabilizing additive by dosing the oil-based fluids with a paraffinic solvent until there is flocculation of the destabilized solids; and extracting a sample from each oil-based fluid after the titration and once the destabilized solids in each oil-based fluid have flocculated; and mixing each extracted sample with a cycloparaffin.

3. The method of claim 2, wherein the step of mixing each extracted sample with a cycloparaffin results in the dispersion of the destabilized solid flocs present in each extracted sample.

4. The method of claim 2, wherein the paraffinic solvent is selected from the group consisting of cetane, heptane, xylene, toluene, hexane, pentane, methylnaphthalene, a paraffinic solvent having a solubility range of about 6.8 to 7.2 $(cal/cm^3)^{1/2}$, and combinations thereof.

5. The method of claim 2, wherein the cycloparaffin is cyclohexane.

6. The method of claim 1, wherein the oil-based fluid is selected from the group consisting of crude oil, fuel oil, atmospheric residua, vacuum, residua, distillation residua, quench oil, visbreaker tar, H-Oil process stream, LC Fining process stream, fluidized catalytic cracker slurry, and combinations thereof.

7. The method of claim 1, wherein the destabilized solids are selected from a group consisting of asphaltenes, polynuclear aromatics, coke, coke precursors, and combinations thereof.

8. The method of claim 1, wherein the field dosage amount ranges from about 1 ppm to about 500 ppm based on the oil-based fluid.

9. The method of claim 1, wherein the step of measuring the change in turbidity over time of each sample to determine a settling rate of the flocculated destabilized solids in each sample is carried out by a turbidity meter.

10. The method of claim 9, wherein the turbidity meter is portable.

11. The method of claim 9, wherein the turbidity meter is in the field.

12. The method of claim 1, further comprising implementing a change to the amount of stabilizing additive applied to the oil-based fluid based upon quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive.

13. The method of claim 1, wherein the step of measuring the change in turbidity over time of each sample to determine a settling rate of the flocculated destabilized solids in each sample is carried out by a nephelometer.

14. The method of claim 13, wherein the nephelometer is portable.

15. The method of claim 1, wherein the field dosage amount ranges from about 10 ppm to about 50 ppm based on the oil-based fluid.

16. The method of claim 1, further comprising implementing a change to a production, transportation, or refining process based upon quantifying the difference between settling rate of the flocculated destabilized solids in the sample of the oil-based fluid having a field dosage amount of stabilizing additive and the settling rate of the flocculated destabilized solids in the sample of the oil-based fluid having no stabilizing additive, the change being selected from a group consisting of: adding an additional feed stream to the oil-based fluid to stabilize the oil-based fluid, adding an additive to the oil-based fluid, adding a different demulsifier to the oil-based fluid than any demulsifier already present in the oil-based fluid, changing a temperature of the oil-based fluid, changing a water feed rate of a unit within the refinery process, and combinations thereof.

* * * * *